United States Patent
Kook et al.

(10) Patent No.: US 9,072,568 B2
(45) Date of Patent: Jul. 7, 2015

(54) ORTHODONTIC SUPPORTING MEMBER

(75) Inventors: Yoon Ah Kook, Seoul (KR); Kyu Rhim Chung, Seoul (KR)

(73) Assignee: Catholic University Industry Academic Cooperation Foundation, Seoul (KR)

(*) Notice: Subject to any disclaimer, the term of this patent is extended or adjusted under 35 U.S.C. 154(b) by 108 days.

(21) Appl. No.: 13/878,045

(22) PCT Filed: Oct. 5, 2010

(86) PCT No.: PCT/KR2010/006773
§ 371 (c)(1),
(2), (4) Date: Apr. 5, 2013

(87) PCT Pub. No.: WO2012/046888
PCT Pub. Date: Apr. 12, 2012

(65) Prior Publication Data
US 2013/0189640 A1  Jul. 25, 2013

(51) Int. Cl.
*A61C 8/00* (2006.01)
*A61C 7/18* (2006.01)
*A61C 7/20* (2006.01)

(52) U.S. Cl.
CPC ............ *A61C 8/0096* (2013.01); *A61C 8/0031* (2013.01); *A61C 7/18* (2013.01); *A61C 7/20* (2013.01)

(58) Field of Classification Search
CPC ............ A61C 5/007; A61C 7/00; A61C 7/10; A61C 8/0031; A61C 8/0096
USPC ................... 433/2, 3, 7, 18, 21, 24; D24/180
See application file for complete search history.

(56) References Cited

U.S. PATENT DOCUMENTS

| | | | | |
|---|---|---|---|---|
| 5,052,930 A * | 10/1991 | Lodde et al. | | 433/173 |
| 5,853,291 A * | 12/1998 | DeVincenzo et al. | | 433/176 |
| 6,827,574 B2 * | 12/2004 | Payton | | 433/8 |
| 7,052,499 B2 * | 5/2006 | Steger et al. | | 606/291 |
| 7,258,545 B2 * | 8/2007 | Hotta | | 433/18 |
| 7,931,469 B1 * | 4/2011 | Schendel | | 433/18 |
| 8,118,850 B2 * | 2/2012 | Marcus | | 606/328 |
| 8,202,089 B2 * | 6/2012 | Dacremont | | 433/173 |
| D712,039 S * | 8/2014 | Lee et al. | | D24/180 |

(Continued)

FOREIGN PATENT DOCUMENTS

| | | |
|---|---|---|
| KR | 100337832 B1 | 5/2002 |
| KR | 100618556 B1 | 9/2006 |

(Continued)

*Primary Examiner* — Cris L Rodriguez
*Assistant Examiner* — Hao D Mai
(74) *Attorney, Agent, or Firm* — The Webb Law Firm

(57) ABSTRACT

A support member for correcting tooth irregularities is provided. The support member includes: a main body that extends in a longitudinal direction and includes a hook portion formed on an end portion thereof; and a plurality of leg portions each of which extends in a radial direction from a central portion of the main body and has a through-hole formed in an end portion thereof, wherein each of the plurality of leg portions is obliquely formed with respect to a line perpendicular to the longitudinal direction of the main body. The support member may be simply fixed to a palatine bone by fixing a fixing screw to the palatine bone without cutting a mucus membrane and may maintain a stable fixed state because the plurality of leg portions are fixed in an area other than a midpalatal suture area.

11 Claims, 5 Drawing Sheets

(56) References Cited

U.S. PATENT DOCUMENTS

| | | | |
|---|---|---|---|
| 8,807,998 B2 * | 8/2014 | Lee | 433/18 |
| 8,992,582 B1 * | 3/2015 | Knoepfle et al. | 606/281 |
| 2003/0104335 A1 * | 6/2003 | Chung | 433/18 |
| 2004/0147931 A1 | 7/2004 | De Clerck | |
| 2006/0069389 A1 * | 3/2006 | Knopfle | 606/61 |
| 2007/0259306 A1 * | 11/2007 | Raines et al. | 433/18 |
| 2010/0047732 A1 | 2/2010 | Park | |

FOREIGN PATENT DOCUMENTS

| | | | |
|---|---|---|---|
| KR | 1020090047759 A | 5/2009 | |
| KR | 1020100138710 A | 12/2010 | |
| WO | WO2009/061079 A1 * | 5/2009 | A61C 7/10 |

* cited by examiner

ORTHODONTIC SUPPORTING MEMBER

BACKGROUND

1. Field of the Invention

The present invention relates to a support member for correcting tooth irregularities, and more particularly, to a support member for correcting tooth irregularities which may be fixed to a palatine bone in an oral cavity by passing a fixing screw through a mucus membrane and fixing the fixing screw to the palatine bone in an area other than a midpalatal suture area without cutting the mucus membrane.

2. Discussion of Related Art

In dental treatment, maxillary and mandibular molars are lost most frequently, and when antagonist teeth are lost, other teeth are extruded, thereby making it difficult to treat the teeth.

In particular, in order to correct molars, anchorage devices are usually fixed in an oral cavity and the molars are corrected using the anchorage devices. In this case, mini implants for correction are often used as the anchorage devices in the oral cavity.

In general, mini implants are implanted on both sides of an alveolar bone, and an elastic body is connected to molars and the mini implants to apply an external force to the molars. In general, for firm fixing, the mini implants have to be disposed in the alveolar bone directly under teeth. Accordingly, roots of the teeth may be damaged during treatment, and it is difficult to accurately adjust positions of the mini implants.

In particular, in order to fix the mini implants in an oral cavity, a mucus membrane has to be cut, and in order to remove the mini implants, the mucus membrane has also to be cut, thereby increasing a burden and risk of surgery for a patient.

SUMMARY OF THE INVENTION

The present invention is directed to providing a support member for correcting tooth irregularities which may be simply fixed to a palatine bone by passing a fixing screw through a mucus membrane and fixing the fixing screw to the palatine bone without cutting the mucus membrane.

The present invention is also directed to providing a support member for correcting tooth irregularities which may fix a fixing screw to a palatine bone area other than a midpalatal suture area and may be fixed to an inside or an outside of an oral cavity to apply an external force to a throat or lips.

One aspect of the present invention provides a support member for correcting tooth irregularities, the support member including: a main body that has a predetermined length and includes hook portions formed on both end portions thereof; and a plurality of leg portions each of which extends in a radial direction from a central portion of the main body, has a through-hole formed in an end portion thereof, is fixed to a palatine bone using a fixing screw that passes through the through-hole, and includes a fixing rib protruding from a surface of the leg portion which is fixed to the palatine bone.

The main body may extend in a longitudinal direction, and each of the plurality of leg portions may obliquely extend at a predetermined angle with respect to a second central line perpendicular to a first central line that extends in the longitudinal direction of the main body.

Each of both end portions of the main body may obliquely extend at a predetermined angle with respect to a central line that halves the main body, wherein each of the plurality of leg portions obliquely extends at a predetermined angle with respect to the central line of the main body.

Another aspect of the present invention provides a support member for correcting tooth irregularities, the support member including: a main body that extends in a longitudinal direction and has a hook portion formed on an end portion thereof; and a plurality of leg portions each of which extends in a radial direction from another end portion of the main body, has a through-hole formed in an end portion thereof, is fixed to a palatine bone using a fixing screw that passes through the through-hole, and includes a fixing rib protruding from a surface of the leg portion which is fixed to the palatine bone, wherein each of the plurality of leg portions obliquely extends at a predetermined angle with respect to a second central line perpendicular to a first central line that extends in the longitudinal direction of the main body.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the exemplary embodiments disclosed below but can be implemented in various forms. The following exemplary embodiments are described in order to enable those of ordinary skill in the art to embody and practice the present invention.

First Exemplary Embodiment

Figure 1:
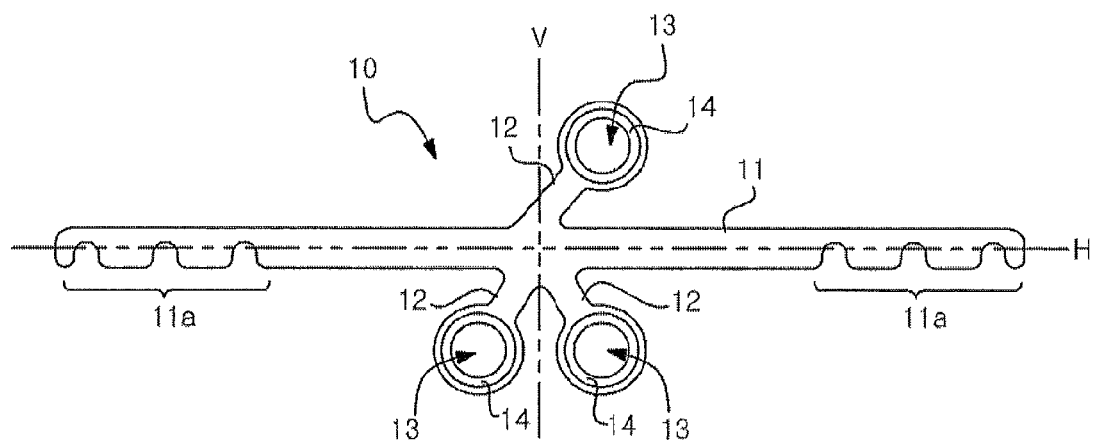
FIGS. 1 and 2 are respectively a top view and a bottom view of a support member for correcting tooth irregularities, according to a first exemplary embodiment of the present invention.
Figure 2:
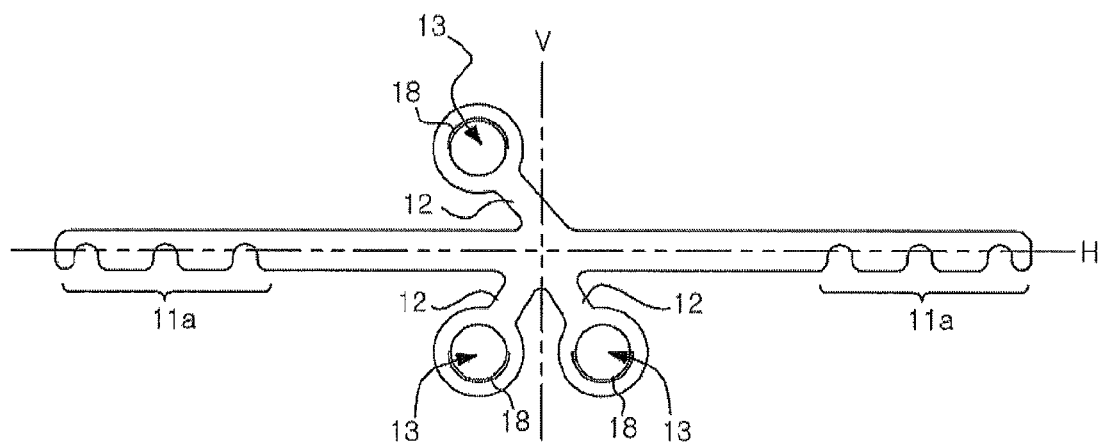
Figure 3:
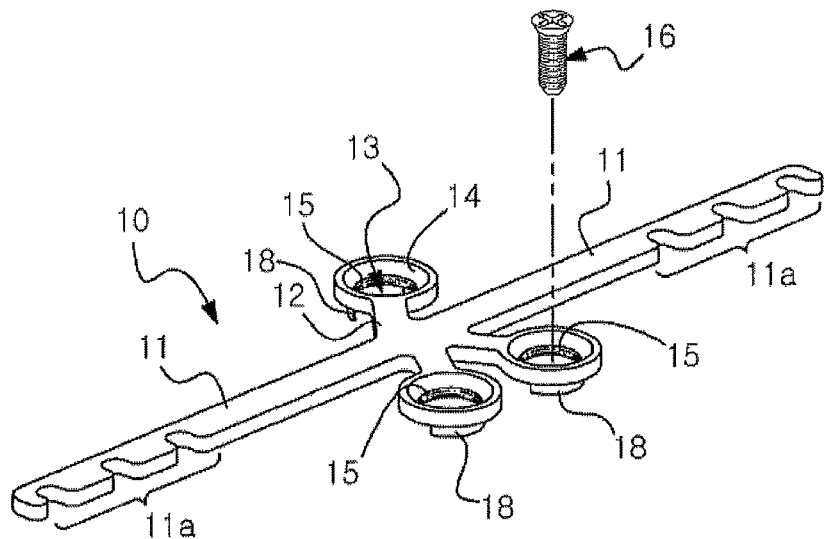
FIGS. 3 and 4 are respectively a top perspective view and a bottom perspective view of the support member according to the first exemplary embodiment of the present invention.
Figure 4:
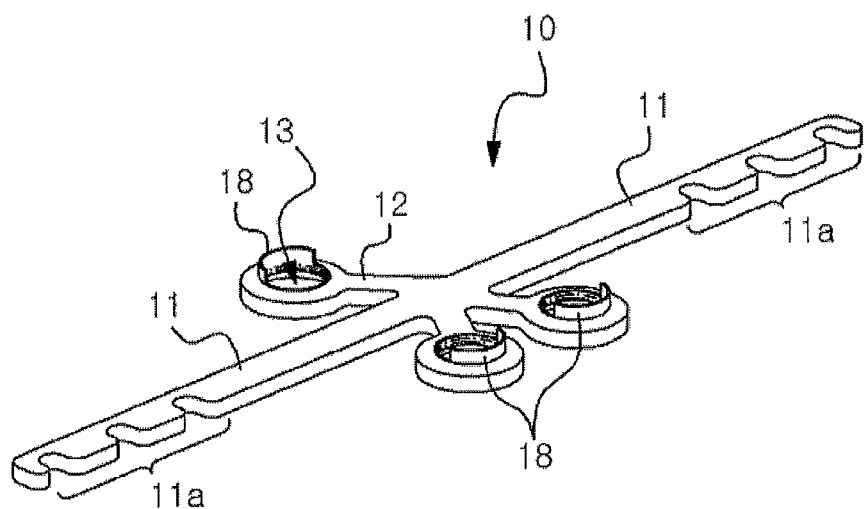

FIGS. 1 and 2 are respectively a top view and a bottom view of a support member 10 for correcting tooth irregularities, according to a first exemplary embodiment of the present invention. FIGS. 3 and 4 are respectively a top perspective view and a bottom perspective view of the support member 10 according to the first exemplary embodiment of the present invention.

The support member 10 according to the first exemplary embodiment includes a main body 11 that straightly extends and has hook portions 11a formed on both end portions thereof, and a plurality of leg portions 12 each of which extends from a central portion of the main body 11 and has a through-hole 13 formed in an end portion thereof.

Each of the leg portions 12 obliquely extends at a predetermined angle with respect to a second central line V perpendicular to a first central line H that extends in a longitudinal direction of the main body 11. Accordingly, as shown in FIGS. 1 and 2, the leg portions 12 are disposed in 3 areas or more of all 4 areas partitioned by the second central line V and the first central line H that extends in the longitudinal direction of the main body 11.

As shown in FIGS. 1 and 2, two adjacent leg portions 12 may symmetrically disposed about the central line V or the first central line H that extends in the longitudinal direction of the main body 11. In this case, the support member 10 fixed to a palatine bone may maintain a further stable fixed state.

A spiral portion 15 to be connected to a fixing screw 16 may be formed on a lower inner circumferential surface of a through-hole 13 of each of the leg portions 12, and a mount groove 14 may be formed in an upper inner circumferential surface of the through-hole 13 of each of the leg portions 12. A head portion of the fixing screw 16 is disposed in the mount groove 14. The mount groove 14 may be formed to have a stepped shape or a tapered surface according to a shape of the head portion of the fixing screw 16.

The mount groove 14 is formed in a top surface of the leg portion 12, and a fixing rib 18 is formed on a bottom surface of the leg portion 12 as shown in FIGS. 2 through 4. The fixing rib 18 protrudes to a predetermined thickness along an outer surface of the through-hole 13 from the bottom surface of the leg portion 12, and has a half-ring shape. The fixing rib 18 is not limited to the half-ring shape and may have a ring shape or a shape obtained by cutting a part of a ring. The fixing rib 18 may have any shape as long as the fixing rib 18 protrudes from the bottom surface of the leg portion 12. Also, the fixing rib 18 may be attached to the leg portion 12 using a processing method such as welding and may be integrally processed and formed with the leg portion 12.

The fixing rib 18 stably fixes the support member 10 to a patient's palatine bone without moving the support member 10 and prevents a part of the support member 10 from being covered due to an inflammation during treatment.

Each of the main body 11 and the leg portion 12 may be formed of any of various materials such as titanium, stainless steel, and gold (Ag). In order to have sufficient strength and minimize inconvenience to the patient, each of the main body 11 and the leg portion 12 may have a thickness of about 1 mm.

The hook portions 11a are formed on both end portions of the main body 11. Each of the hook portions 11a by which an elastic body B (see FIG. 5) is caught may be at least one notch formed in a side portion of both end portions of the main body 11.

A process of fixing the support member 10 constructed as described above to the palatine bone in an oral cavity and a principle for correcting tooth irregularities will now be explained with reference to FIGS. 1 through 5.

Figure 5:
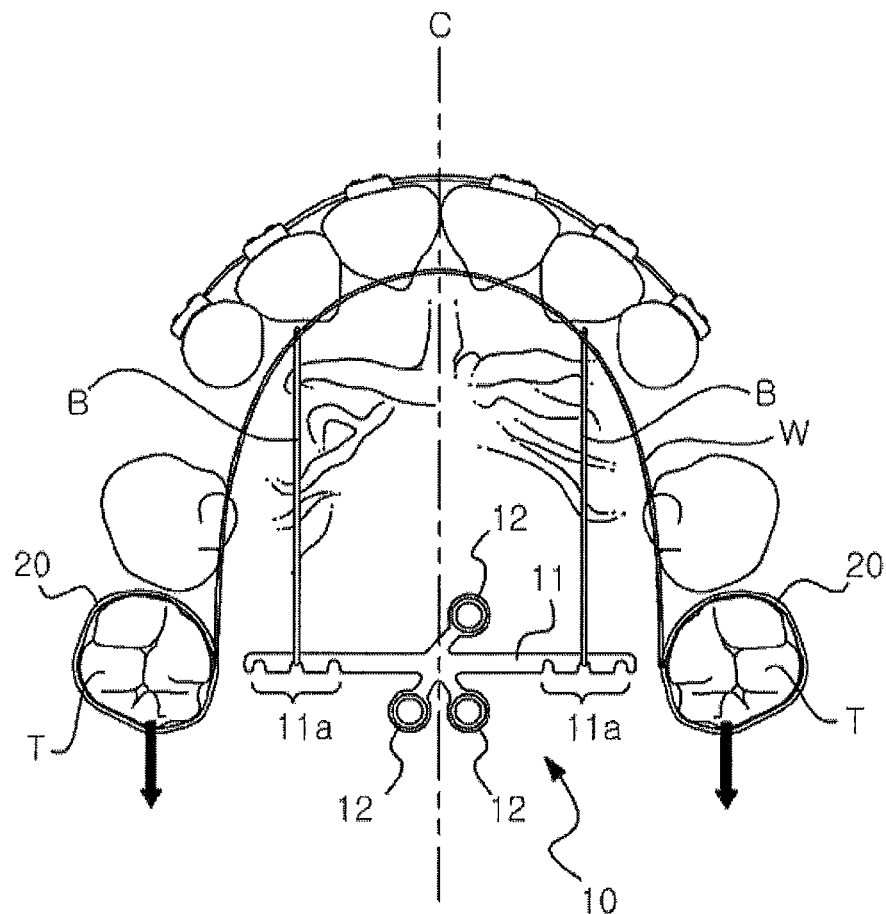
FIGS. 5 is a view illustrating a state where the support member according to the first exemplary embodiment of the present invention is provided in an oral cavity.

FIG. 5 is a view illustrating a state where the support member 10 according to the first exemplary embodiment of the present invention is fixed to the palatine bone.

First, when teeth, for example, molars T on both sides in the oral cavity, are to be corrected, fixtures 20 are mounted to surround the molars T and are connected to each other using a wire W having a U-shape.

Next, the support member 10 is fixed to a palate, that is, the palatine bone. That is, in a state where the support member 10 is disposed such that a vertical central line V and a midpalatal suture area C coincide, the fixing screw 16 corresponds to the through-hole 13 of each of the leg portions 12. In this case, the support member 10 may be first fixed to the palatine bone using the fixing rib 18. Next, when the fixing screw 16 is rotated, the fixing screw 16 passes through a mucus membrane and is fixed to the palatine bone, and thus the support member 10 is fixed to the palatine bone in a state where each of the leg portions 12 is exposed.

Since the plurality of leg portions 12 are arranged as described above, each of the leg portions 12 which has been fixed to the palatine bone using the fixing screw 16 does not correspond to the midpalatal suture area C of the oral cavity, and thus a state where the support member 10, more particularly, the main body 11, is closely attached to the palate may be maintained.

In a state where the support member 10 is fixed to the palatine bone, the elastic body B is connected to the hook portion 11a of the main body 11 and the wire W. As shown in FIG. 5, the elastic body B is disposed in a notch constituting the hook portion 11a, and thus even when a certain amount of external force is applied to the elastic body B, the elastic body B is not separated from the hook portion 11a.

In the state of FIG. 5, an elastic force of the elastic body B is applied to the hook portion 11a of the main body 11 and thus is transmitted to the molars T through the wire W and the fixtures 20. As a result, a correction force is applied in an arrow direction of FIG. 5, thereby making it possible to perform a correction process.

The support member 10 constructed as described above may be fixed by passing the fixing screw 16 through the through-hole 13 of each of the leg portions 12 and the mucus membrane and fixing the fixing screw 16 to the palatine bone without cutting the mucus membrane.

Also, since each of the leg portions 12 is fixed to an area other than the midpalatal suture area C that protrudes, the support member 10 may maintain a stable fixed state.

Second Exemplary Embodiment

Figure 6:
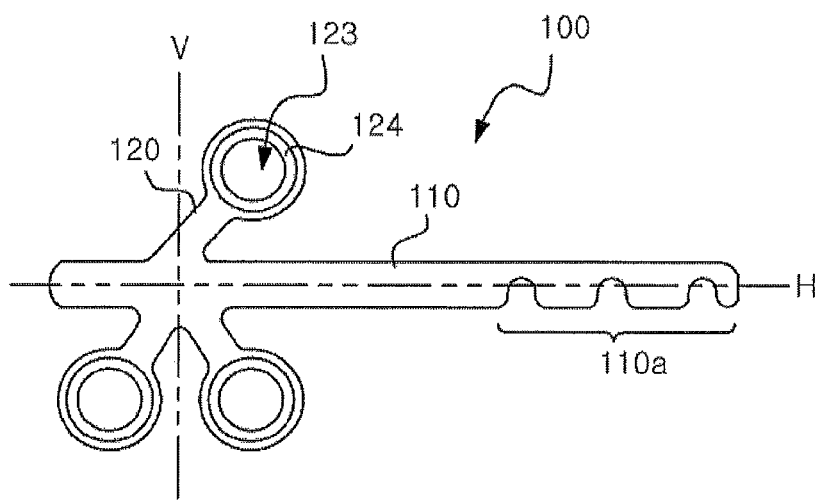
FIG. 6 is a top view illustrating a support member for correcting tooth irregularities, according to a second exemplary embodiment of the present invention.

FIG. 6 is a top view of a support member 100 for correcting tooth irregularities, according to a second exemplary embodiment of the present invention. An overall structure of the support member 100, a process of providing the support member 100, and a function of the support member 100 of the present embodiment are the same as those of the support member 10 of FIGS. 1 through 4.

The support member 100 of the present exemplary embodiment is characterized in that a hook portion 110a is formed on an end portion of a main body 110, and a plurality of leg portions 120 radially extend on another end portion of the main body 110.

Each of the leg portions 120 obliquely extends at a predetermined angle with respect to the second central line V perpendicular to the first central line H that extends in a longitudinal direction of the main body 110.

Unlike the support member 10 according to the first exemplary embodiment, the support member 100 of the present exemplary embodiment is constructed such that the hook portion 110a is formed only on an end portion of the main body 110. The support member 100 of the present exemplary embodiment may be used to correct one molar.

Although a notch formed only on a side portion (that is, a portion corresponding to a throat) of the main body 11 or 110 is used as the hook portion 11a or 110a formed on both end portions or on one end portion of the main body 11 or 110 in FIGS. 1 through 4 or 6, the present invention is not limited thereto.

That is, by forming a notch on both side portions (that is, a portion corresponding to the throat and a portion corresponding to lips) of the main body 11 or 110 as the hook portion 11a or 110a formed on both end portions or on one end portion of the main body 11 or 110, a dentist may use the support member 10 or 100 irrespective of a position of the notch.

Third Exemplary Embodiment

As shown in FIG. 5, the support member 10 or 100 may be used to correct tooth irregularities by applying an external force to the molars T toward the throat. However, in order to apply an external force to the molars T in an opposite direction, that is, toward lips, the wire W that connects the fixtures 20 mounted on the molars T has to be disposed on a portion around the throat instead of the lips.

Also, an elastic force of the elastic body B may be applied to the fixtures 20 only when there is a sufficient distance between the wire W that connects the fixtures 20 and the hook portion 11a or 110a of the support member 10 or 100.

To this end, the support member 10 or 100 may be fixed to a portion of the palatine bone close to the lips instead of the throat. However, since a width of an area close to the lips is less than a width of an area close to the throat due to a structure of the oral cavity, it is not preferable to use the support member 10 according to the first exemplary embodiment of the present invention in this case.

Figure 7:
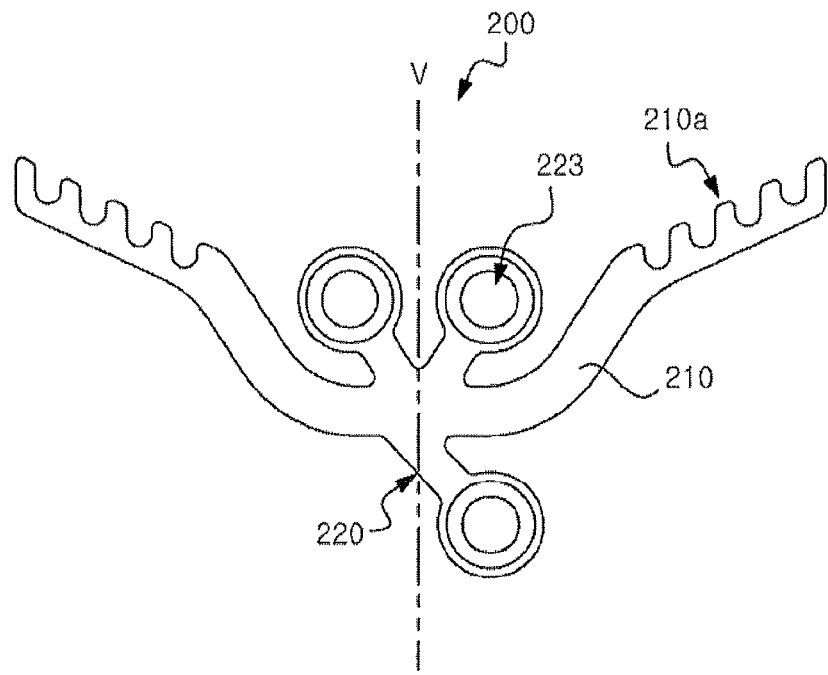
FIG. 7 is a top view illustrating a support member for correcting tooth irregularities, according to a third exemplary embodiment of the present invention.

FIG. 7 is a top view of a support member 200 for correcting tooth irregularities by applying an external force to a molar toward lips, according to a third exemplary embodiment of the present invention.

The support member 200 according to the third exemplary embodiment of the present invention includes a main body 210 that has hook portions 210a formed on both end portions thereof, and a plurality of leg portions 220 each of which extends from a central portion of the main body 210 and has a through-hole 223 formed in an end portion thereof.

Figure 8:
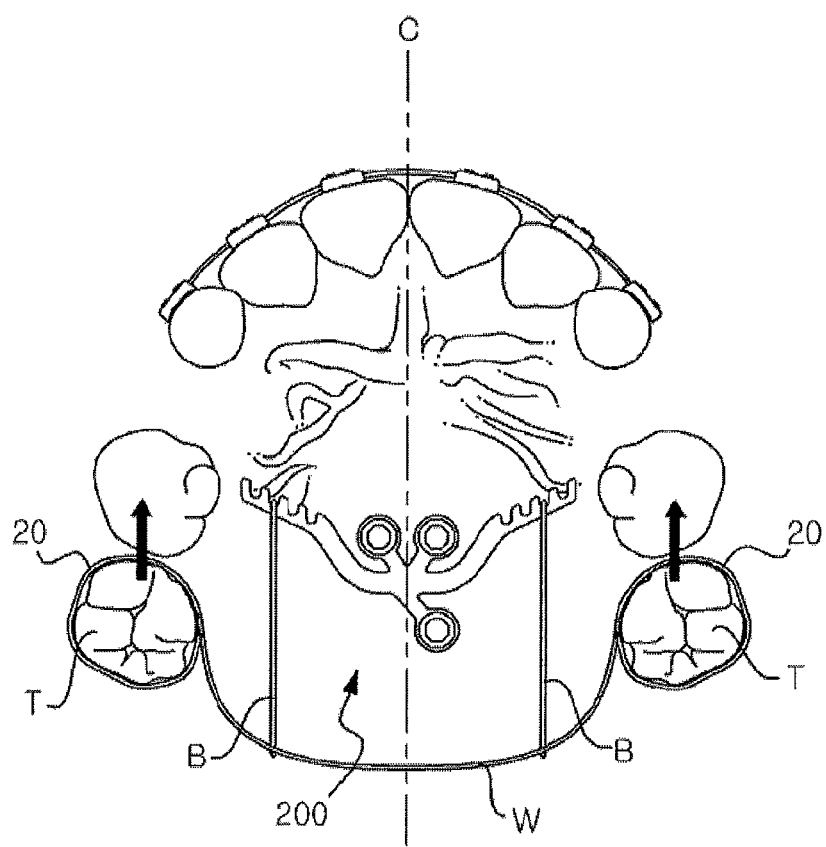
FIGS. 8 and 9 are views illustrating states where the support member according to the third exemplary embodiment of the present invention is provided in the oral cavity.

Each of both end portions of the main body 210 obliquely extends at a predetermined angle with respect to the vertical central line V that halves the main body 210. The both end portions of the main body 210 extend in the same direction, preferably, toward the lips as shown in FIG. 8. Accordingly, the both end portions of the main body 210 have an obtuse angle less than 180° therebetween.

In this structure, even when the main body 210 has the same length as that of the main body 11 of the support member 10 according to the first exemplary embodiment, an overall width of the support member 200 is much less than that of the support member 10 according to the first exemplary embodiment.

Each of the leg portions 220 obliquely extends at a predetermined angle with respect to the central line V of the main body 210. Accordingly, as shown in FIG. 7, the leg portions 220 are disposed at both sides of the vertical central line V.

Materials, detailed structures, arrangement, and functions of the leg portions 220 of the support member 200, and detailed structures, arrangement, and functions of the hook portions 210a formed on the both end portions of the main body 210 according to the third exemplary embodiment are the same as those of the leg portions 12 or 120 and the hook portions 11a or 110a of the support member 10 or 100 according to the first or second exemplary embodiment, and thus an explanation thereof will not be given.

A process of fixing the support member 200 constructed as described above to the palatine bone and a principle for correcting tooth irregularities will be explained with reference to FIGS. 7 and 8.

Figure 9:
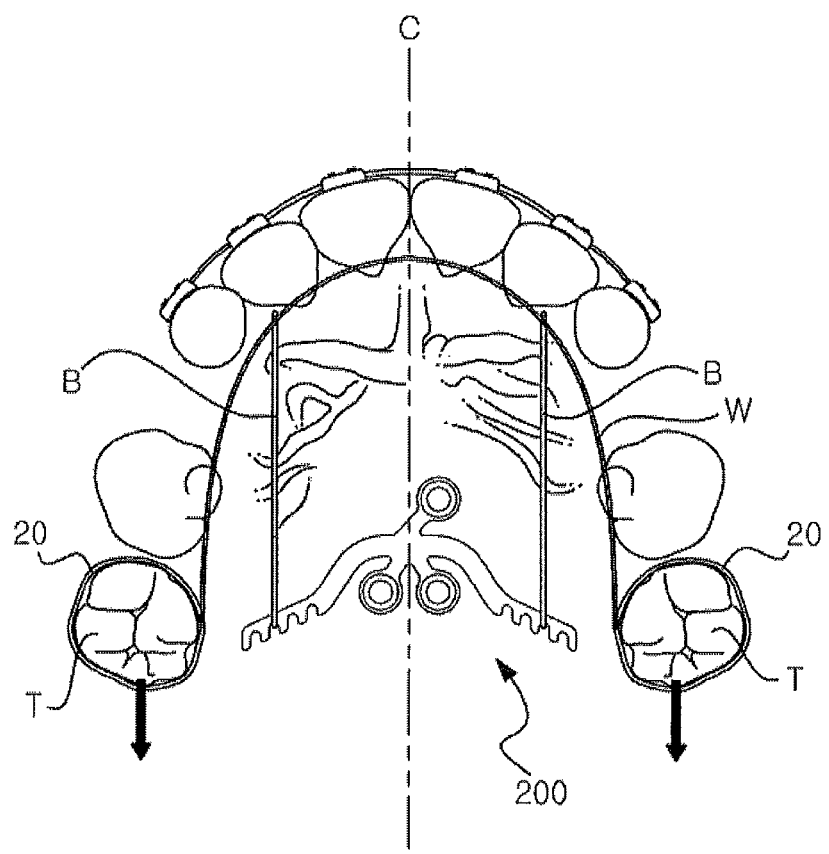

FIGS. 8 and 9 are views illustrating states where the support member 200 according to the third exemplary embodiment of the present invention is fixed to the palatine bone.

First, as shown in FIG. 8, when the molars T on both sides of the oral cavity are to be corrected toward lips, the fixtures 20 are mounted to surround the molars T and are connected to each other using the wire W having a U-shape. In this case, the fixtures 20 are disposed at an area close to the throat.

Next, the support member 200 is fixed to the palate, that is, the palatine bone. That is, in a state where the support member 200 is disposed such that the vertical central line V and the midpalatal suture area C coincide, the fixing screw 16 (see FIG. 5) corresponds to the through-hole 223 of each of the leg portions 220. Next, when the fixing screw 16 is rotated, the fixing screw 16 passes through the mucus membrane and is fixed to the palatine bone, and thus the support member 200 is fixed to the palatine bone in a state where each of the leg portions 220 is exposed.

In a state where the support member 200 is fixed to the palatine bone, the elastic body B is connected to the hook portion 210a of the main body 210 and the wire W. As shown in FIG. 8, the elastic body B is disposed in a notch constituting the hook portion 210a, and thus even when a certain amount of external force is applied to the elastic body B, the elastic body B is not separated from the hook portion 210a.

In the state of FIG. 8, an elastic force of the elastic body B is applied to the hook portion 210a of the main body 210 and thus is transmitted to the molars T through the wire W and the fixtures 20. As a result, a correction force is applied toward the lips, that is, in an arrow direction of FIG. 8, thereby making it possible to perform a correction process.

Also, according to the third exemplary embodiment, correction may be performed by applying a correction force to the molars T toward the throat, as shown in FIG. 9. Referring to FIG. 9, the support member 200 is arranged in an opposite direction to that in FIG. 8, and thus a correction process is performed by applying a correction force to the molars T toward the throat.

Although the hook portions 210a, that is, notches, formed on the both end portions of the main body 210 are formed only on a portion corresponding to the lips in FIGS. 7 and 8 illustrating the most preferable embodiment, the hook portions 210a may be formed on an opposite portion, that is, a portion corresponding to the throat.

A support member for correcting tooth irregularities according to the present invention may be simply fixed to a palatine bone by passing a fixing screw through a mucus membrane and fixing the fixing screw to the palatine bone without cutting the mucus membrane.

In particular, since a leg portion which is an element of the present invention is fixed in an area other than a midpalatal suture area, the support member may maintain a stable fixed state.

Also, since a fixing rib is formed on the leg portion, the support member may be stably fixed to the palatine bone without moving, and a part of the support member may be prevented from being covered due to an inflammation during treatment.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A support member for correcting tooth irregularities, the support member comprising:
   a main body having a first end portion and a second end portion, that has a predetermined length and comprises hook portions formed on both end portions thereof; and
   a plurality of leg portions each of which extends in a radial direction from a central portion of the main body, having a through-hole formed in an end portion of the plurality of leg portions, the plurality of leg portions configured to be fixed to a palatine bone using a fixing screw that passes through the through-hole, and the through-hole comprises a fixing rib protruding from a surface of the leg portion which is configured to be fixed to the palatine bone, wherein the fixing rib has a half-ring shape, wherein each of the plurality of leg portions obliquely extends at a predetermined angle with respect to a second central line perpendicular to a first central line that extends in the longitudinal direction of the main body, wherein the plurality of leg portions are disposed in three of four areas partitioned by the second central line and the first central line that extends in the longitudinal direction of the main body, and wherein the through-hole comprises a spiral portion that is formed on a lower inner circumferential surface of the through-hole.

2. The support member of claim 1, wherein the main body extends in a longitudinal direction.

3. The support member of claim 2, wherein two adjacent leg portions are symmetrically disposed about at least one line of the second central line and the first central line that extends in the longitudinal direction of the main body.

4. The support member of claim 1, wherein each of both end portions of the main body obliquely extends at a predetermined angle with respect to a central line that halves the main body, wherein each of the plurality of leg portions obliquely extends at a predetermined angle with respect to the central line of the main body.

5. The support member of claim 1, wherein each of the hook portions is at least one notch formed in at least one side portion of an end portion of the main body.

6. The support member of claim 1, wherein the through-hole comprises a mount groove that is formed in an upper inner circumferential surface of the through-hole.

7. The support member of claim 1, wherein each of the main body and the plurality of leg portions is formed of any one of titanium, stainless steel, and gold.

8. A support member for correcting tooth irregularities, the support member comprising:

a main body that extends in a longitudinal direction and has a hook portion formed on an end portion thereof; and a plurality of leg portions each of which extends in a radial direction from another end portion of the main body, the plurality of leg portions have a through-hole formed in an end portion thereof, the plurality of leg portions are configured to be fixed to a palatine bone using a fixing screw that passes through the through-hole, and the through-hole comprises a fixing rib protruding from a surface of the leg portion which is configured to be fixed to the palatine bone, wherein each of the plurality of leg portions obliquely extends at a predetermined angle with respect to a second central line perpendicular to a first central line that extends in the longitudinal direction of the main body, wherein the fixing rib has a half-ring shaped, wherein the plurality of leg portions are disposed in three of four areas partitioned by the second central line and the first central line that extends in the longitudinal directions of the main body, and wherein the through-hole comprises a spiral portion that is formed on a lower inner circumferential surface of the through-hole.

9. The support member of claim 8, wherein the hook portion is at least one notch formed in at least one side portion of the end portion of the main body.

10. The support member of claim 8, wherein the through-hole comprises a mount groove that is formed in an upper inner circumferential surface of the through-hole.

11. The support member of claim 8, wherein each of the main body and of the plurality of leg portions is formed of any one of titanium, stainless steel, and gold.

* * * * *

UNITED STATES PATENT AND TRADEMARK OFFICE
CERTIFICATE OF CORRECTION

PATENT NO.       : 9,072,568 B2
APPLICATION NO.  : 13/878045
DATED            : July 7, 2015
INVENTOR(S)      : Yoon Ah Kook et al.

Page 1 of 1

It is certified that error appears in the above-identified patent and that said Letters Patent is hereby corrected as shown below:

In the Claims

Column 6, Line 60, Claim 1, delete "body" and insert -- body, --

Column 8, Line 19, Claim 8, delete "shaped," and insert -- shape, --

Column 8, Lines 22-23, Claim 8, delete "directions" and insert -- direction --

Signed and Sealed this
Nineteenth Day of July, 2016

Michelle K. Lee
*Director of the United States Patent and Trademark Office*